United States Patent
Niyaz et al.

(10) Patent No.: US 6,903,219 B2
(45) Date of Patent: Jun. 7, 2005

(54) PROCESS TO PRODUCE DERIVATIVES FROM UK-2A DERIVATIVES

(75) Inventors: Noormohamed Mohamed Niyaz, Indianapolis, IN (US); Carl Vincent DeAmicis, Indianapolis, IN (US); Richard Brewer Rogers, Mobile, AL (US); Kevin Gerald Meyer, Zionsville, IN (US); William Hunter Dent, III, Indianapolis, IN (US); Peter Biagio Anzeveno, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/491,978
(22) PCT Filed: Oct. 4, 2002
(86) PCT No.: PCT/US02/31848

§ 371 (c)(1),
(2), (4) Date: Apr. 5, 2004

(87) PCT Pub. No.: WO03/031403

PCT Pub. Date: Apr. 17, 2003

(65) Prior Publication Data

US 2004/0186296 A1 Sep. 23, 2004

Related U.S. Application Data

(60) Provisional application No. 60/327,547, filed on Oct. 5, 2001.

(51) Int. Cl.$^7$ .............................................. C07D 407/12
(52) U.S. Cl. .................................................... 546/281.7
(58) Field of Search ....................................... 546/281.7

(56) References Cited

PUBLICATIONS

Ueki, M., et al., "UK–2A, B, C and D Noveml Antifungal Antibiotics from *Streptomyces* sp. 517–02" Journal of Antibiotics vol. 49, No. 7 p. 639–643 (1996).

*Primary Examiner*—Patricia L. Morris
(74) *Attorney, Agent, or Firm*—Lynn Zettler

(57) ABSTRACT

A process to produce alkyl ethers from UK-2A derivatives is provided. Additionally, alkyl ether derivatives of UK-2A are provided.

1 Claim, No Drawings

PROCESS TO PRODUCE DERIVATIVES FROM UK-2A DERIVATIVES

This application claims the benefit of provisional application 60/327,547 filed on Oct. 5, 2001.

FIELD OF THE INVENTION

This invention is related to the field of processes used to produce alkyl ethers from UK-2A derivatives. This invention is also related to the field of alkyl ether derivatives of UK-2A.

BACKGROUND OF THE INVENTION

UK-2A is a natural product having the following formula.

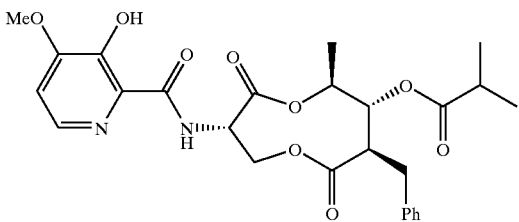

UK-2A is described in M. Ueki, et al *J. Antibiot.* 1996, 49, 639. While this compound has certain properties that make it useful in a variety of fields, currently, it is being investigated as a starting point for making compounds that have efficacy in the fungicide area.

DETAILED DESCRIPTION OF THE INVENTION

As used herein, the terms alkyl, alkoxy, alkenyl, and alkynyl shall include both branched and unbranched carbon atom chains.

As used herein, the terms alkenyl, alkynyl, and cycloalkenyl shall contain one or more unsaturated carbon-carbon bonds.

As used herein, the term "aryl" shall mean phenyl or naphthyl.

As used herein, the term "heteroaryl" shall mean any 5 or 6 membered aromatic ring, containing one or more heteroatoms, where such heteroatoms are selected from the group consisting of O, N, and S, and where the remaining atoms of the aromatic ring are carbon atoms. Suitable examples include, but are not limited to pyridine, pyridazine, pyrimidine, pyrazine, pyrrole, pyrazole, imidazole, furan, thiophene, oxazole, isoxazole, thiazole, isothiazole, and thiadiazole.

As used herein, the term:

"Me" shall mean methyl ($CH_3$);
"Et" shall mean ethyl ($CH_2CH_3$);
"Pr" shall mean propyl ($CH_2CH_2CH_3$);
"Bu" shall mean butyl ($CH_2CH_2CH_2CH_3$);
"Ph" shall mean phenyl ($C_6H_5$);
"ppm" shall mean parts per million;
"psi" shall mean pounds per square inch;
"m.p." shall mean the melting point;
"b.p." shall mean the boiling point;
"IG" shall mean a gas that is substantially inert under the reaction conditions disclosed herein, suitable examples are argon, nitrogen, and helium;
"RT" shall mean ambient room temperature;
"dppf" shall mean 1,1'-bis(diphenylphosphino)ferrocene;
"dppb" shall mean 1,4-bis(diphenylphosphino)butane;
"$Pd_2dba_3$" shall mean tris-dibenzylideneacetonedipalladium(0);
"$Pd(PPh_3)_4$" shall mean tetrakis-triphenylphosphinepalladium(0); and
"$Pd_2dba_4$" shall mean tetrakis-dibenzylideneacetonedipalladium(0);

Throughout this document, all temperatures are given in degrees Celsius (° C.) and all percentages are weight percentages, unless otherwise stated.

In Reaction One, Compound A is reacted with Compound B to produce Compound C. This reaction is conducted in the presence of a suitable catalyst, a suitable ligand, and a suitable solvent.

Reaction One

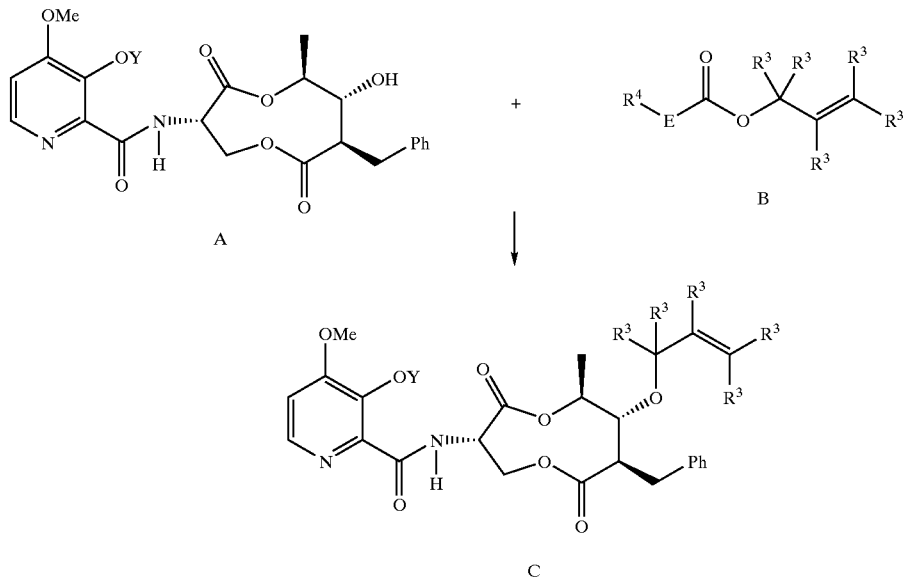

In Reaction Two, Compound C is reduced to produce Compound D.

Reaction Two

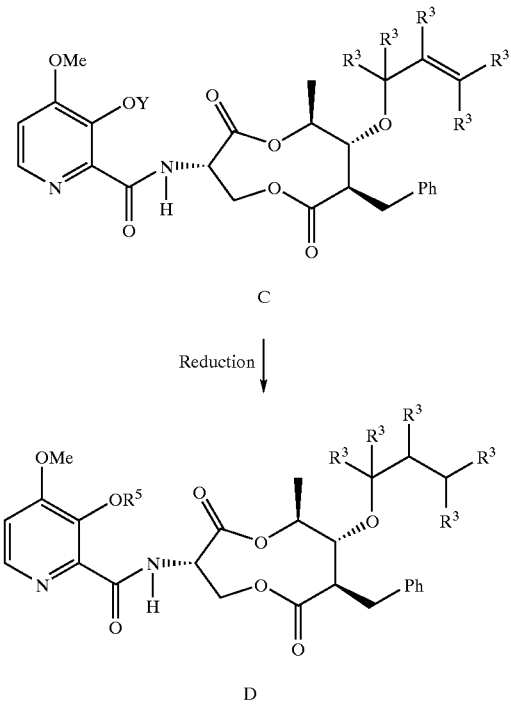

C

Reduction ↓

D

In Compounds A, B, C, and D:
E is selected from the group consisting of O and $NR^6$;
Y is selected from the group consisting of H, benzyl, $Si(C_1-C_4 \text{ alkyl})_3$, $Si(Ph)_r(C_1-C_4 \text{ alkyl})_{(3-r)}$ (r=1, 2, or 3), $SO_2R$, $C(R^1R^2)OR$, $C(R^1R^2)OC(O)XR$, $C(R^{1-2}R^{2-1})OR$, and $C(R^{1-2}R^{2-1})OC(O)XR$, and $C(O)XR$;
X is selected from the group consisting of O, S, and a bond;
R is selected from the group consisting of $C_1-C_8$ alkyl, $C_2-C_8$ alkenyl, $C_2-C_8$ alkynyl, $C_3-C_8$ cycloalkyl, aryl, and heteroaryl;
$R^1$ is selected from the group consisting of H, $C_1-C_6$ alkyl, $C_1-C_6$ alkoxy, $C_3-C_6$ cycloalkyl, aryl, and heteroaryl;
$R^2$ is selected from the group consisting of H, $C_1-C_6$ alkyl, $C_1-C_6$ alkoxy, $C_3-C_6$ cycloalkyl, aryl, and heteroaryl;
$C(R^{1-2}R^{2-1})$ is a 3 to 6 membered ring, where the members of the ring are selected from the group consisting of C, O, and S;
$R^3$ is independently selected from the group consisting of H, $C_1-C_6$ alkyl, $C_2-C_6$ alkenyl, $C_2-C_6$ alkynyl, $C_3-C_7$ cycloalkyl, aryl, and heteroaryl;
$R^4$ is selected from the group consisting of $C_1-C_{10}$ alkyl and aryl;
$R^5$ is selected from the group consisting of Y and members of Y that have been reduced;
$R^6$ is selected from the group consisting of $C_1-C_6$ alkyl and aryl;
wherein each of the alkyl, alkoxy, alkenyl, alkynyl, cycloalkyl, cycloalkenyl, benzyl, aryl, heteroaryl, and $R^{1-2}R^{2-1}$ may be substituted with one or more substituents.

The substituents can be any substituent that does not substantially interfere with the transfer of the allylic group from Compound B to the non-aromatic hydroxy group of Compound A.

Examples of the substituents include, but are not limited to, the group consisting of $C_1-C_6$ alkyl, $C_1-C_6$ alkoxy, $C_2-C_6$ alkenyl, $C_2-C_6$ alkynyl, $C_3-C_6$ cycloalkyl, $C_5-C_6$ cycloalkenyl, aryl, heteroaryl, halo, $C_2-C_6$ alkenoxy, $C_3-C_6$ cycloalkoxy, aryloxy, heteroaryloxy, aryl $C_1-C_6$ alkyloxy, aryl $C_1-C_6$ alkyl, acyloxy, acyl $C_1-C_6$ alkyloxyamino, $C_1-C_6$ alkylacyloxy, nitro, hydroxy, and $C_1-C_6$ alkylsulfonyl.

These substituents may also be substituted with substituents selected from group consisting of $C_1-C_6$ alkyl, $C_1-C_6$ alkoxy, $C_2-C_6$ alkenyl, $C_2-C_6$ alkynyl, $C_3-C_6$ cycloalkyl, $C_5-C_6$ cycloalkenyl, aryl, heteroaryl, halo, $C_2-C_6$ alkenoxy, $C_3-C_6$ cycloalkoxy, aryloxy, heteroaryloxy, aryl $C_1-C_6$ alkyloxy, aryl $C_1-C_6$ alkyl, acyloxy, acyl $C_1-C_6$ alkyloxyamino, $C_1-C_6$ alkylacyloxy, nitro, hydroxy, and $C_1-C_6$ alkylsulfonyl.

Specific examples of substituents are (mono or poly, chloro or fluoro) alkyl, benzyl, and benzyloxy.

Sometimes it is desirable that if one or more $R^3$'s has more than two carbon atoms, then at least two of the other $R^3$'s are H.

Sometimes it is desirable to use heteroaryl or aryl substituents that are fused together with other aryl or heteroaryl substituents.

A suitable catalyst is any catalyst that can facilitate the transfer of the allylic group from Compound B to the non-aromatic hydroxy group of Compound A. Suitable catalysts can be selected from, but are not limited to, the group consisting of Pd(II) acetate, $Pd_2dba_3$, $Pd(PPh_3)_4$, $Pd_2dba_4$, and $Rh(PPh_3)_2Cl_2$. In general, the amount of catalyst to use is from about 0.25 mol percent to about 5 mol percent based upon Compound A.

A suitable ligand is any ligand that can help the catalyst facilitate the transfer of the allylic group from Compound B to the hydroxy group of Compound A. Suitable ligands can be selected from, but are not limited to, the group consisting of $PPh_3$, $Ph_2P(CH_2)_nPPh_2$ (where n is 3, 4, or 5), tri(o-tolyl) phosphine, trifurylphosphine, triphenylarsine, dppb, and dppf. In general, the amount of ligand to use is from about 1 mol percent to about 20 mol percent based upon Compound A.

A suitable solvent is any aprotic solvent that facilitates the reaction. Suitable solvents can be selected from, but are not limited to, N,N-dimethylformamide, methyl-t-butyl ether, diglyme, heptane, acetonitrile, ethyl acetate, 1,2-dichloroethane, benzene, N-methylpyrolidinone, hexamethylphosphoramide, tetrahydrofuran, and 1,2-dimethoxyethane. Additionally, mixtures of suitable solvents may be used. Additionally, substituted forms of the suitable solvents, such as substituted benzene may be used, where the appropriate substituents are selected from those indicated earlier.

Each reaction is conducted at any temperature that facilitates the transfer of the allylic group from Compound B to the hydroxy group of Compound A. Usually, this temperature is above 40° C. but equal to or below the boiling point of the reaction mixture.

EXAMPLES

These examples are provided to further illustrate the invention, but are not meant to limit the invention to these specific examples.

PREPARATION OF COMPOUNDS 1–4

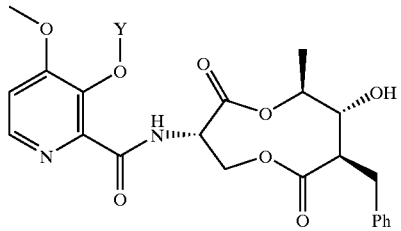

wherein

| COMPOUND NUMBER | Y |
|---|---|
| 1 | H |
| 2 | Benzyl |
| 3 | CH$_2$OC(O)CH$_3$ |
| 4 | C(O)CH$_3$ |

N-[(3S,7R,8R,9S)-7-benzyl-8-hydroxy-9-methyl-2, 6-dioxo-1,5-dioxonan-3-yl]-3-hydroxy-4-methoxypyridine-2-carboxamide (Compound 1)

Diisobutylaluminum hydride (1.5 M in toluene, 23.3 mmol) was added dropwise to a 15° C. solution of natural product UK-2A (5.8 mmol, 3.0 g) in toluene (60 mL). The mixture was stirred an additional 15 min and quenched with EtOAc (20 mL). Hydrochloric acid (2N, 100 mL) was added slowly and stirred vigorously for 15 min. The layers were separated and the organic layer dried (MgSO$_4$) and concentrated in vacuo to give 1.82 g (70%) of Compound 1 as a foamy, light yellow solid. Exact Mass: m/z calcd. for C$_{22}$H$_{24}$N$_2$O$_8$ [M]$^+$=44.1533, found 444.1513. $^1$H-NMR data was consistent for Compound 1.

(3S,6S,7R,8R)-8-benzyl-3-({[3-(benzyloxy)-4-methoxypyridin-2-yl]carbonyl}amino)-6-methyl-4,9-dioxo-1,5-dioxonan-7-yl 2-methylpropanoate (Compound 2)

Benzyl bromide (23.5 mL) was added to a solution of NaI (11.3 mol, 1.68 g) in acetone (60 mL). Compound 1 (22.5 mmol, 10 g) was added followed by powdered K$_2$CO$_3$.(38.8 mol, 5.3 g) and the mixture stirred vigorously overnight. The mixture was diluted with EtOAc (150 mL) and washed with H$_2$O (2×150 mL). The organic layer was dried (MgSO$_4$), and concentrated in vacuo. Purification via column chromatography (acetone/hexanes) gave 4.70 g (39%) of Compound 2 as an off-white solid. $^1$H-NMR and MS (M+1)$^+$= 535 were consistent for Compound 2.

Preparation of ({2-[({(3S,7R,8R,9S)-7-benzyl-8-(hydroxy)-9-methyl-2,6-dioxo-1,5-dioxonan-3-yl}amino)carbonyl]-4-methoxypyridine-3-yl}oxy) methyl acetate (Compound 3)

To a solution of Compound 1 (40 g, 90.09 mmol) in dry acetone (360 mL) was added powdered potassium carbonate (14.92 g, 108 mmol) in three portions over 5 min, the mixture stirred at 0–5° C. for 20 min and sodium iodide (2.697 g, 18 mmol) was added. Bromomethyl acetate (16.54 g, 108.11 mmol) was then added dropwise over 15 min using an addition funnel, the mixture stirred at 0–5° C. for 1 h then at RT for 3 hours. The mixture was diluted with ethyl acetate (700 mL) and water (200 mL), the organic phase rinsed with water (×2), brine. (×2), dried over sodium sulfate and concentrated in vacuo to give a solid, which was passed through silica gel (1:1 hexanes/acetone) to give 42 g of Compound 3. (M+1)$^+$=517. Spectral data were consistent with the assigned structure.

Preparation of ({2-[({(3S,7R,8R,9S)-8-(hydroxy)-7-benzyl-9-methyl-2,6-dioxo-1,5-dioxonan-3-yl}amino)carbonyl]-4-methoxypyridine-3-yl}oxy) acetate (Compound 4)

To an ice-cold solution of the Compound 1 (20.0 g, 45.0 mmol), 4-N,N-dimethylaminopyridine (55 mg, 0.45 mmol) and pyridine (7.12 g, 90 mmol) in dry methylene chloride (90 mL) was added acetyl chloride (3.71 g, 47.25 mmol), dropwise over 5 min, and the mixture stirred at 0–5° C. for 1 hour. The mixture was concentrated on a rotary evaporator to a volume of ca. 20 mL and diluted with ethyl acetate (250 mL) and 1N aq. HCl (100 mL). The organic phase was removed, rinsed successively with water (75 mL×2), brine (50 mL×2), dried with anhydrous sodium sulfate, and concentrated on a rotary evaporator to give 21.0 g (96% yield) of a white solid. MS: (M+1)$^+$=487. (M−1)$^+$=485. Spectral data were consistent with the assigned structure.

PREPARATION OF COMPOUNDS 5–10 USING REACTION ONE

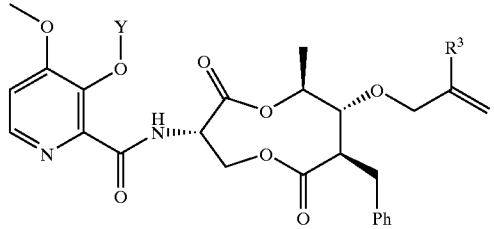

wherein

| COMPOUND NUMBER | Y | R$^3$ |
|---|---|---|
| 5 | Benzyl | CH$_3$ |
| 6 | CH$_2$OC(O)CH$_3$ | CH$_3$ |
| 7 | Benzyl | H |
| 8 | CH$_2$OC(O)CH$_3$ | H |
| 9 | C(O)CH$_3$ | H |
| 10 | H | H |

GENERAL PROCEDURE

An oven-dried round bottom flask (1 L), equipped with a mechanical stirrer, an addition funnel, a reflux condenser, an IG inlet tube, and a thermometer, was charged with Compound A (about 100 parts by mole, for example, 0.04 moles), an aprotic solvent (about 200 mL) to form a reaction mixture. This reaction mixture was then purged with IG for about 0.5 hours.

In an oven dried round bottom flask (100 mL) a suitable ligand (about 10 parts by mole) and a suitable catalyst (about 2.5 parts by mole) were dissolved in an aprotic solvent (about 50 mL, pre-purged with IG) to form a catalyst solution. The catalyst solution was then transferred (under IG) to the reaction mixture via a cannula.

The addition funnel was then charged with an aprotic solvent (about 15 mL, pre-purged with IG) and Compound B (about 120 parts by mole, pre-purged with IG) to form an allyl carbonate solution. This solution was then added dropwise to the reaction mixture over the next 1.5 hours. During this dropwise addition the reaction mixture was being heated at about 60° C. After this dropwise addition, an aliquot of the reaction mixture was drawn and analyzed by HPLC and LC-MS. This analysis indicated that substantially all of Compound A had disappeared.

The reaction mixture was then cooled to RT and concentrated on a rotary evaporator, under vacuum, to produce a foam. This foam was then dissolved in $CH_2Cl_2$ (about 40 mL). This solution was then loaded onto a bed of silica gel (about 120 g, 230–400 mesh) and eluted with mixtures of hexane and acetone (1L) to give a 40–85% yield of Compound C.

Preparation of N-{(3S,7R,8R,9S)-7-benzyl-9-methyl-8-[(2-methylprop-2-enyl)oxy]-2,6-dioxo-1,5-dioxonan-3-yl}-3-(benzyloxy)-4-methoxypyridine-2-carboxamide (Compound Compound 5 was prepared in 72% yield using Compound 2 (20.0 g, 37.45 mmol), dppf (2.08 g, 3.78 mmol), $Pd_2dba_3$ (0.857 g, 0.936 mmol), and ethyl methallylcarbonate (7.12 g, 44.94 mmol). Purification by flash column chromatography on silica gel and eluting with mixtures of hexane and acetone gave a white solid. m.p.=50–52° C. Spectral data were consistent with the assigned structure.

Preparation of ({2-[({(3S,7R,8R,9S)-7-benzyl-9-methyl-8-[(2-methylprop-2-enyl)oxy]-2,6-dioxo-1,5-dioxonan-3-yl}amino)carbonyl]-4-methoxypyridine-3-yl }oxy)methyl acetate (Compound 6)

Compound 6 was prepared in 40% yield using Compound 3 (13.4 g, 25.97 mmol) with dppf (1.44 g, 2.60 mmol), $Pd_2dba_3$ (0.59 g, 0.65 mmol) and ethyl methallylcarbonate (4.87 g, 33.8 mmol). Filtration through a bed of silica gel (hexane-acetone) afforded a white solid, which upon recrystallization from toluene gave white tetragonal crystals: m.p.=102–104° C. Spectral data were consistent with the assigned structure.

Preparation of N-{(3S,7R,8R,9S)-8-(allyloxy)-7-benzyl-9-methyl-2,6-dioxo-1,5-dioxonan-3-yl}-3-(benzyloxy)-4-methoxypyridine-2-carboxamide (Compound 7)

Compound 7 was prepared in 69% yield using Compound 2 (65.2 g, 122.1 mmol) with dppb (5.20 g, 12.21 mmol), $Pd_2dba_3$ (2.79 g, 3.05 mmol) and ethyl methallylcarbonate (20.63 g, 158.73 mmol). Crude product upon chromatography on silica gel eluting with a mixture of hexane-acetone (1:1) afforded a white foam: m.p.=55–57° C., MS: (M+1)$^+$= 585, (M-1)$^+$=583. Spectral data were consistent with the assigned structure.

Preparation of ({2-[({(3S,7R,8R,9S)-8-(allyloxy)-7-benzyl-9-methyl-2,6-dioxo-1,5-dioxonan-3-yl}amino)carbonyl]-4-methoxypyridine-3-yl}oxy) methyl acetate (Compound 8)

Compound 8 was prepared in 68% yield using Compound 3 (150 mg, 0.29 mmol) with dppb (12 mg, 0.03 mmol), $Pd_2dba_3$ (5.30 mg, 0.006 mmol) and ethyl methallylcarbonate (41 mg, 0.31 mmol). Purification by flash column chromatography on silica gel eluting with a mixture of hexane-acetone (1:1) gave a white foam: MS: (M+1)$^+$=557, (M-1)+=555. Spectral data were consistent with the assigned structure.

Preparation of ({2-[({(3S,7R,8R,9S)-8-(allyloxy)-7-benzyl-9-methyl-2,6-dioxo-1,5-dioxonan-3-yl}amino)carbonyl]-4-methoxypyridine-3-yl}oxy) acetate (Compound 9)

Compound 9 was prepared in 56% yield using Compound 4 (18.08 g, 37.2 mmol) with dppf (2.06 g, 3.70 mmol), $Pd_2dba_3$ (851 mg, 0.93 mmol) and allyl ethyl carbonate (5.81 g, 44.64 mmol). Purification by flash column chromatography on silica gel eluting with a mixture of hexane-ethyl acetate (3:1) gave a white foam: MS: (M+1)$^+$=527, (M-1)$^+$= 525. Spectral data were consistent with the assigned structure.

Preparation of N-[((3S,7R,8R,9S)-8-allyloxy-7-benzyl-9-methyl-2,6-dioxo-1,5-dioxonan-3-yl}-3-hydroxy-4-methoxypyridine-2-carboxamide (Compound 10)

Compound 10 was prepared in 61% yield using Compound 1 (1.2 g, 2.7 mmol) with dppf (122 mg, 0.27 mmol), $Pd_2dba_3$ (50 mg, 0.054 mmol) and allyl ethyl carbonate (440 mg, 3.24 mmol). Purification by flash column chromatography on silica gel eluting with a mixture of hexane-ethyl acetate (3:1) gave a white foam: MS: (M+1)$^+$=485, (M-1)+= 483. Spectral data were consistent with the assigned structure.

PREPARATION OF COMPOUNDS 11–14 USING REACTION TWO

| COMPOUND NUMBER | Y | $R^3$ |
|---|---|---|
| 11 | H | $CH_3$ |
| 12 | $CH_2OC(O)CH_3$ | $CH_3$ |
| 13 | H | H |
| 14 | $C(O)CH_3$ | H |

GENERAL PROCEDURE

Compound C was dissolved in ethyl acetate in a Parr bottle, about 10% wt palladium on charcoal about 10% wt of substrate) added and the mixture shaken under hydrogen atmosphere (about 1 to 50 psi) for about 1.5 hours. The mixture was purged with nitrogen, the catalyst was removed by filtration and the filtrate concentrated on a rotary evaporator. The solid reside was recrystallized from appropriate solvent system to give 85–98% yield of Compound D.

Preparation of N-[((3s,7R,8R,9S)-7-benzyl-8-isobutoxy-9-methyl-2,6-dioxo-1,5-dioxonan-3-yl}-3-hydroxy-4-methoxypyridine-2-carboxamide (Compound 11)

Compound 11 was prepared in 81% yield using Compound 5 (15.8 g, 29.5 mmol) with 10% palladium on charcoal (2.5 g) and hydrogen (40 psi) in ethyl acetate (200 mL) for 1.5 hours. Recrystallization from hot toluene (40 mL) gave white needles: m.p. 168–169° C. Spectral data were consistent with the assigned structure.

Preparation of {[2-({[(3S,7R,8R,9S)-7-benzyl-8-isobutoxy-9-methyl-2,6-dioxo-1,5-dioxonan-3-yl}amino)carbonyl]-4-methoxypyridine-3-yl}oxy) methyl acetate (Compound 12)

Compound 12 was prepared in 95% yield using Compound 6 (6.0 g, 10.5 mmol) with 10% palladium on charcoal (1.2 g) and hydrogen (40 psi) in ethyl acetate (150 mL) for 1.5 hour. Recrystallization from a mixture of hot methylcyclohexane and toluene (4:1) gave 5.7 g of white needles: m.p.134–136° C. Spectral data were consistent with the assigned structure.

Preparation of N-[((3S,7R,8R,9S)-7-benzyl-9-methyl-2,6-dioxo-8-propoxy-1,5-dioxonan-3-yl}-3-hydroxy-4-methoxypyridine-2-carboxamide (Compound 13)

Compound 13 was prepared in 94% yield using Compound 7 (47.7 g, 81.0 mmol) and 10% palladium on charcoal (3.5 g) in ethyl acetate (400 mL) for 1 hours. Recrystallization from a 2:1 mixture of toluene/methylcyclohexane afforded white needles: m. p. 150–152° C. Spectral data were consistent with the assigned structure.

Preparation of {[2-({[(3S,7R,8R,9S)-7-benzyl-8-propoxy-9-methyl-2,6-dioxo-1,5-dioxonan-3-yl}amino)carbonyl]-4-methoxypyridine-3-yl}oxyacetate (Compound 14)

The Compound 14 was prepared in 99% yield using Compound 9 (2.0 g, 3.8 mmol) and 10% palladium on charcoal (200 mg) in ethyl acetate (60 mL) for 1 hour. Recrystallization from a 2:1 mixture of toluene/methylcyclohexane afforded white needles: m. p. 132–133° C. Spectral data were consistent with the assigned structure.

We claim:

1. A process comprising reacting Compound A with Compound B to produce Compound C,

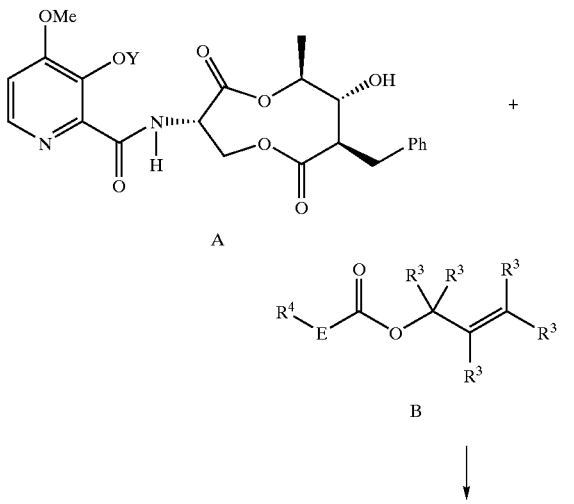

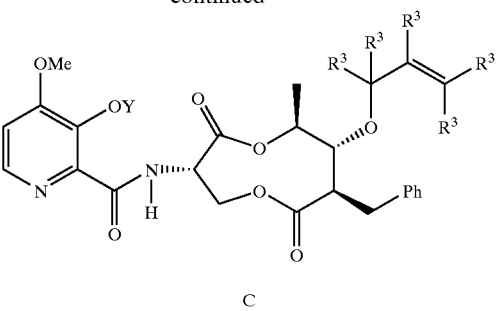

wherein the reaction is conducted in the presence of a catalyst that can facilitate the transfer of the allylic group from Compound B to the non-aromatic hydroxy group of Compound A, a ligand that can help the catalyst facilitate the transfer of the allylic group from Compound B to the hydroxy group of Compound A, and a solvent that is an aprotic solvent that facilitates the reaction; at a temperature that facilitates the transfer of the allylic group from comoound B to the hydroxy group of Compound A and wherein E is selected from the group consisting of O and $NR^6$;

Y is selected from the group consisting of H, benzyl, $Si(C_{1-4}$ alkyl$)_3$, $Si(Ph)_r(C_{1-4}$ alkyl$)_{(3-r)}$(r=1, 2, or 3), $SO_2R$, $C(R^1R^2)OR$, $C(R^1R^2)OC(O)XR$, $C(R^{1-2}R^{2-1})OR$, and $C(R^{1-2}R^{2-1})OC(O)XR$, and $C(O)XR$;

X is selected from the group consisting of O, S, and a bond;

R is selected from the group consisting of $C_1$–$C_8$ alkyl, $C_2$–$C_8$ alkenyl, $C_2$–$C_8$ alkynyl, $C_3$–$C_8$ cycloalkyl, aryl, and heteroaryl;

$R^1$ is selected from the group consisting of H, $C_1$–$C_6$ alkyl, $C_1$–$C_6$ alkoxy, $C_3$–$C_6$ cycloalkyl, aryl, and heteroaryl;

$R^2$ is selected from the group consisting of H, $C_1$–$C_6$ alkyl, $C_1$–$C_6$ alkoxy, $C_3$–$C_6$ cycloalkyl, aryl, and heteroaryl;

$C(R^{1-2}R^{2-1})$ is a 3 to 6 membered ring, where the members of the ring are selected from the group consisting of C, O, and S;

$R^3$ is independently selected from the group consisting of H, $C_1$–$C_6$ alkyl, $C_2$–$C_6$ alkenyl, $C_2$–$C_6$ alkynyl, $C_3$–$C_7$ cycloalkyl, aryl, and heteroaryl;

$R^4$ is selected from the group consisting of $C_1$–$C_{10}$ alkyl and aryl;

$R^6$ is selected from the group consisting of $C_1$–$C_6$ alkyl and aryl; and wherein each of the alkyl, alkoxy, alkenyl, alkynyl, cycloalkyl, cycloalkenyl, benzyl, aryl, heteroaryl, and $R^{1-2}R^{2-1}$ may be substituted with one or more substituents.

* * * * *